United States Patent [19]

Cameron et al.

[11] Patent Number: 5,431,875
[45] Date of Patent: Jul. 11, 1995

[54] DENTAL ALLOY PRODUCING LIGHT OXIDES

[75] Inventors: Thomas B. Cameron, Windsor; Edward F. Smith, III, Madison, both of Conn.

[73] Assignee: The J. M. Ney Company, Bloomfield, Conn.

[21] Appl. No.: 236,465

[22] Filed: May 2, 1994

[51] Int. Cl.6 .............................................. C22C 5/00
[52] U.S. Cl. ..................................... 420/463; 420/465; 148/442; 433/207; 433/208; 433/228.1
[58] Field of Search ............... 420/463, 465; 148/442; 433/208, 207, 228.1

[56] References Cited

U.S. PATENT DOCUMENTS

| | | |
|---|---|---|
| 3,819,366 | 6/1974 | Katz . |
| 3,928,913 | 12/1975 | Schaffer . |
| 3,929,474 | 12/1975 | Ingersoll . |
| 3,929,475 | 12/1975 | Ingersoll . |
| 4,205,982 | 6/1980 | German . |
| 4,350,526 | 9/1982 | Schaffer . |
| 4,387,072 | 6/1983 | Schaffer . |
| 4,518,564 | 5/1985 | Prasad . |
| 4,527,979 | 7/1985 | McLean et al. . |
| 4,539,177 | 9/1985 | Prasad . |
| 4,659,384 | 4/1987 | Daigo et al. . |
| 4,943,483 | 7/1990 | Ingersoll et al. . |
| 4,992,297 | 2/1991 | van der Zel . |
| 5,298,218 | 3/1994 | Groll et al. . |

FOREIGN PATENT DOCUMENTS

| | | |
|---|---|---|
| 3146794 | 6/1983 | Germany . |
| 3414575 | 7/1985 | Germany . |

*Primary Examiner*—Deborah Yee

[57] ABSTRACT

A precious metal alloy for dental restorations which develops a light oxide upon firing, on a percentage weight basis at makeup, consists of 60–95 precious metal(s) selected from the group consisting of 60–855 palladium, 0–10 gold, 0–10 platinum, 0–12 silver, and mixtures thereof; 1–15 tin; 2–7 zinc; 0.005–0.2 boron; 0–2 gallium; 0–2 cobalt; 0–15 indium; 0–0.2 of a deoxidant selected from the group consisting of silicon, germanium, magnesium, aluminum, lithium, tantalum and mixtures thereof; and 0–1.0 of a grain refiner selected from the group consisting of ruthenium, iridium, rhenium, and mixtures thereof. The alloy has a liquidus temperature of not more than 1400° C., and the alloy has a tensile yield strength of at least 250 Mpa and an elongation of at least 2 percent. Restorations having a porcelain coating fired on castings of the alloy evidence a light oxide color.

19 Claims, No Drawings

DENTAL ALLOY PRODUCING LIGHT OXIDES

BACKGROUND OF THE INVENTION

The present invention relates to precious metal alloys and, more particularly, to such alloys which are used for making dental restorations.

Alloys utilized for making dental restorations are required to have a high degree of biocompatability or inertness when exposed to the conditions in the mouth, and good physical properties so that they will provide a long lived restoration. In addition, they should not adversely affect the color of the porcelain coating which is fired thereon so that the restoration will blend with the appearance of the natural teeth.

For many years, gold and platinum alloys had been utilized for such restorations, but the escalating costs of those metals produced a trend toward use of non-noble metal alloys and to use in precious metal alloys of palladium which was considerably lower in cost. Initially, palladium/silver alloys were favored because of their lower cost and simulation of the appearance of platinum alloys. However, some palladium/silver alloys exhibited a tendency to discolor the porcelain coatings fired thereon, i.e., the so called "greening" effect. Illustrative of palladium/silver alloys for dental restorations are those described in Schaffer U.S. Pat. No. 4,350,526 and Ingersoll U.S. Pat. Nos. 3,929,474 and 3,929,475.

Schaffer U.S. Pat. No. 4,387,072 addressed the greening problem by a silver-free alloy which essentially included palladium, gallium and copper or cobalt. Alloys of this type were highly successful in replacing palladium/silver alloys because they did not demonstrate the greening effect. Unfortunately, this alloy has a tendency to produce a dark oxide during firing of the porcelain and this dark oxide may produce an undesirable effect in trying to match the restoration and the natural teeth.

Recently, Groll et al U.S. Pat. No. 5,298,218 has attempted to address the dark oxide problem by incorporating with in a palladium/gold alloy and 9-14 percent by weight of modifying elements comprising gallium, tin, and indium with a number of other metals as optional additives. Although the patentees indicate a substantial improvement in the darkness of the oxide based upon apparent visual comparison, the oxide formed on the surface of the casting during porcelain firing still is relatively dark and has a tendency to discolor some translucent porcelains.

Accordingly, it is an object of the present invention to provide a novel precious metal alloy for dental restorations which will form a light colored oxide during firing.

It is also an object to provide such an alloy which exhibits a good balance of properties and which may be easily cast.

Another object is to provide a dental restoration utilizing a casting of the novel alloy and no readily discernible discoloration of the porcelain by the oxide film formed on the casting.

SUMMARY

It has now been found that the foregoing and related objects may be readily attained in a precious metal alloy for dental restorations which develops a light oxide upon firing. The alloy, on a percentage weight basis at makeup, consists essentially of 60-95 precious metal(s) selected from the group consisting of 60-85 palladium, 0-10 gold, 0-10 platinum, 0-12 silver, and mixtures thereof; 1-15 tin; 2-7 zinc; 0.005-0.2 boron; 0-2 gallium; 0-2 cobalt; 0-15 indium; 0-0.2 of a deoxidant selected from the group consisting of silicon, germanium, magnesium, aluminum, lithium, tantalum and mixtures thereof; and 0-1.0 of a grain refiner selected from the group consisting of ruthenium, iridium, rhenium, and mixtures thereof. The alloy has a liquidus temperature of not more than 1400° C., and castings of the alloy have a tensile yield strength of at least 250 Mpa and an elongation of at least 2 percent.

In the preferred alloys, the precious metal component comprises 65-72 palladium, 1-5 gold, 8-12 silver, and mixtures thereof. The other components comprise 8-12 tin, 3-7 zinc, 0.03-0.1 boron, 0-2 gallium, 0.5-4.0 indium, and 0.05-0.3 of a grain refiner selected from the group consisting of ruthenium, iridium, rhenium, and mixtures thereof.

Desirably, the grain refiner is ruthenium, and gallium, when used, is present in the amount of 0.2-1.0 percent.

Castings of the alloy are made and a restoration is made by firing a translucent porcelain coating on the casting. This coating evidences a light coloration and is free from discoloration.

DETAILED DESCRIPTION OF THE PREFERRED EMBODIMENTS

As described in the preceding section, the novel precious metal alloys of the present invention utilize palladium as the principal component and essentially contain tin, zinc and boron as modifying elements. Optionally, the precious metal content may include small amounts of gold, silver and platinum. Other optional modifying elements include gallium, cobalt and indium, a number of other elements as deoxidants, and grain refiners. The total precious metal content should not exceed 95 percent and may be as low as 65 percent.

More specifically, the alloy of the present invention contains a total of 60-95 percent precious metals which essentially must include 60-85 percent palladium. The precious metal component may contain up to 10 percent gold, up to 10 percent platinum and up to 12 percent silver. Exceeding 12 percent of silver will have a tendency to produce partial greening, in some porcelains which are more sensitive to the silver content, but it is helpful from the standpoint of adjusting thermal expansion. Platinum will allow adjustment downwardly of thermal expansion, but it also increases the liquidus. Gold allows adjustment of physical properties. Preferably, the precious metal component will contain 65-72 percent palladium and the gold content will be 1-5 percent, the silver content 8-12 percent. If platinum is substituted, the combined gold and platinum content should not exceed 6 percent. Increasing the gold and platinum content above 6 percent may adversely effect the melting range and will certainly increase the cost of the alloy.

Tin is present in the range of 1-15 percent and is found to contribute to the strength and hardness of the alloy, favorably control its thermal expansion and contribute to the formation of the desired light oxide. Preferably, it is present in an amount of 8-12 percent.

Zinc is included in the range of 2-7 percent and has a significant effect in forming a light oxide, and also it favorably affects strength, hardness and melting range. However, exceeding 7 percent may have an adverse effect because zinc oxide at higher levels is less adherent than is desirable for the porcelain firing operation. Preferably, it is present in the range of 2-7 percent.

Boron has been found to have a very significant affect upon the lightness of the oxide film and it also functions as a contributor to the hardness of the alloy and as a scavenger of oxygen. Generally, it is present in an amount of at least 0.005 percent and up to 0.2 percent; preferably, it should be in the range of 0.03-0.1 percent. Care should be taken during initial makeup of the alloy so that the boron component is not totally oxidized in the initial melting.

Turning next to the optional components, indium may be included in the amount of up to 5 percent. It contributes to hardness and tends to produce a light oxide; preferably, when used, it is in the range of 0.5-4.0 percent.

Gallium may be included in an amount of up to 2 percent to strengthen and harden the alloy, and to maintain a desirable melting point range; however, it forms a dark oxide. Similarly, cobalt may be used in an amount of up to 2 percent because of its tendency to strengthen and harden the alloy, and to maintain a desirable melting point range. However, it also produces a dark oxide.

Minor amounts of deoxidants from the group of silicon, germanium, magnesium, aluminum, lithium, tantalum may also be incorporated in the alloy, but controlled conditions of casting and the presence of boron minimize the need therefor.

A grain refiner is desirable to minimize segregation during casting and to increase the tensile strength of the alloy. Ruthenium, iridium, rhenium and mixtures thereof have been found highly beneficial in amounts of up to 1 percent, and preferably in the range of 0.05-0.3 percent. Of the several grain refining elements, ruthenium has been found preferably in the specified alloy composition.

A preferred alloy of the present invention contains 65-72 percent palladium, 1-5 percent gold, 8-12 percent silver, 8-12 percent tin, 3-7 percent zinc, 0.03-0.1 percent boron, 0.5-4 percent indium, and 0.05-0.3 percent of a grain refiner.

The several components should be adjusted within the ranges indicated to ensure that the alloy has a liquidus temperature of not more than 1400° to facilitate casting, and exhibits a tensile yield strength (0.2 percent) of at least 250 Mpa (36,300 psi) and a tensile elongation of at least 2 percent.

As indicated hereinbefore, the components of the alloy composition should be adjusted to produce the following properties:

Tensile yield strength (at 0.2 percent offset) of heat treated specimens of at least 250 Mpa (36,300 psi) using the method of ANSI/ADA Specification No. 38 (1991)

Tensile elongation at failure of heat treated specimens of at least 2 percent using the method of ANSI/ADA Specification No. 38 (1991).

A liquidus temperature of not more than 1400° C. using the cooling curve method.

The coefficient of thermal expansion (25°-500° C.) desirably should be at least $13.5 \times 10^{-5/°}$ C., although some recently developed porcelains permit use of a lower value.

To provide an objective measurement of the lightness of the oxide which is formed on the casting, a spectrophotometer is employed with the CIELAB System developed by the International Committee on Illumination (CIE) and described in "COLOR TECHNOLOGY FOR JEWELRY ALLOY APPLICATIONS" by D. P. Agarwal and G. Raykhteaum, in the *Santa Fe Symposium on Jewelry Manufacturing Technology*, 1988, published by Met-Chem Research, Inc, Boulder, Colo. in 1989.

In the CIELAB System, the spectrophotometer is utilized to measure the value L* based upon standards supplied with the instrument with white having a relative value of 100 and black having a relative value of 0.

The alloy is melted using conventional dental casting techniques by torch or electric methods and cast into an investment. The shape of the casting is a flat plate approximately 2.5 cm (one inch) square and 1.5 mm (0.06 inch) thick. The surface of the plate is ground flat using abrasives and at least 0.15 mm (0.006 inch) is removed from the surface. The surface is then ground using dental hand grinding equipment to render the surface similar to that of a dental restoration prior to heat treatment. The plates are heated in a dental furnace typically used for firing porcelain at a temperature of 1010° C. (1850F.), held at temperature for 5 minutes in air and then removed from the furnace to cool in air.

The sample surfaces must be kept clean prior to measurement. The measurement of sample lightness is made using a spectrophotometer (Diano Match Scan DTM 1045) under CWF illumination (cool white Fluorescent). Measurements are made using the CIELAB L*, a*, b* values. The information is quantitatively expressed as three variables; L* indicating the light-dark relationship, a* giving the red-green relationship, and b* giving the yellow-blue relationship. However, the L* measurement is the only component used to quantify the lightness of the sample. The greater the L* value, the lighter the sample. An average of three readings is taken on each sample.

For the present invention, alloys having an L* value of at least 54 as determined above are desirable.

Illustrative of the beneficial effect of the zinc content upon the lightness (L*) of the oxide film are the data set forth in the following Table One:

TABLE ONE

| | EFFECT OF ZINC ON LIGHTNESS | | | | | | | | | | |
|---|---|---|---|---|---|---|---|---|---|---|---|
| Sample | PD | AU | AG | IN | GA | RU | IR | PT | ZN | SN | L* |
| A | 69.7 | 1 | 11.5 | 4 | — | 0.2 | — | — | 3.8 | 9.8 | 55 |
| B | 69.7 | 3 | 9.8 | 4 | — | 0.2 | — | — | 3.5 | 9.8 | 54.5 |
| C | 76 | 0 | 0 | 10 | 0 | 0.25 | — | 6 | 0 | 7.75 | 52.5 |
| D | 76 | 0 | 6 | 10 | 0 | 0.25 | — | — | 0 | 7.75 | 53.2 |
| E | 71 | 5 | 7 | — | 1 | 0.2 | — | — | 5.8 | 10 | 55.98 |
| F | 70 | 5 | 8 | — | 2 | 0.2 | — | — | 4.8 | 10 | 55.3 |

Illustrative of the beneficial effect of the boron content upon the lightness (L*) of the oxide film are the data set forth in the following Table Two:

TABLE TWO

| Sample | EFFECT OF BORON ON LIGHTNESS | | | | | | | | | | |
| --- | --- | --- | --- | --- | --- | --- | --- | --- | --- | --- | --- |
| | PD | AU | AG | IN | GA | RU | IR | ZN | SN | B | L* |
| A | 72 | 5 | 6 | — | 0 | 0.2 | — | 4.8 | 12 | 0 | 54.4 |
| B | 71 | 3 | 9.61 | 2 | 0.4 | 0.03 | — | 4.54 | 9.4 | 0.02 | 56.8 |
| C | 70.2 | 3 | 9.77 | 2 | 0.05 | — | — | 5.04 | 9.88 | 0.06 | 56.3 |
| D | 69.7 | 3 | 9.7 | 2 | — | 0.2 | — | 5.5 | 9.8 | 0.1 | 61.9 |
| E | 69 | 4 | 8.85 | 5.5 | — | — | 0.2 | 4 | 8.25 | 0.2 | 68.1 |

Illustrative of the present invention is the following specific example wherein all parts are parts by weight unless otherwise indicated. An alloy is prepared by melting under reducing atmosphere from components, providing at makeup, 69.8 percent palladium, 3 percent gold, 9.7 percent silver, 2 percent indium, 5.04 percent zinc, 9.8 percent tin, 0.5 percent gallium, 0.06 percent boron and 0.1 percent ruthenium. The solidus temperature of this alloy is determined to be 1174° C., the liquidus temperature is determined to be 1321° C.

Tensile specimens of the alloy are found to have a tensile elongation of 12 percent and an offset yield strength (at 0.2 percent offset) of 690 Mpa (100,000 psi) and an ultimate tensile strength of 1035 Mpa (150,000 psi) following a heat treatment at 1010° C. for 10 minutes in vacuum and then air cooling. The modulus of elasticity is measured at 117,000 Mpa (17,000,000 psi).

A cast specimen is found to have a Vickers hardness of 255, and the density is 113 dwt/in$^3$. Thermal expansion is measured at $14 \times 10^{-6}$° C. over the range of 25 to 500 at a rate of 3° C. per minute.

Three castings for lightness measurement are made and tested for the lightness of the oxide coating using the procedure employed is that previously described in the specification. The value of L* is found to average 56.9.

A sample 3 unit bridge restoration is prepared using this alloy and a porcelain sold under the trademark CERAMCO II by Ceramco. The firing conditions are in accordance with the manufacturers specifications.

The bridge restoration was ground and then conditioned by preheating the framework in front of a 1200° F. (650° C.) muffle for two minutes. It was then placed inside the muffle and the temperature was raised to 1850° F. (1010° C.) at 100° F. (55° C.) per minute in air. The sample was then removed from the furnace immediately. The oxide was light gray in color.

The dental porcelain was applied using the multi-step coating and firing procedures outlined by the manufacturer. After firing, no discoloration was observed. No cracking was observed indicating that the alloy is compatible with the color requirements and expansion characteristics of the porcelain.

Thus, it can be seen from the foregoing detailed specification that the novel precious metal alloy of the present invention develops a light oxide upon heating which does not discolor the porcelain fired thereon to produce a dental restoration. The alloy exhibits a good balance of properties to enable facile processing.

Having thus described the invention what is claimed is:

1. A precious metal alloy for dental restorations which develops a light oxide upon firing, said alloy, on a percentage weight basis at makeup, consisting essentially of:
    (a) 60-95 total amount of precious metal(s) selected from the group consisting of 60-85 palladium, 0-5 gold, 0-10 platinum, 0-12 silver, and mixtures thereof;
    (b) 1-15 tin;
    (c) 2-7 zinc;
    (d) 0.005-0.2 boron;
    (e) 0-2 gallium;
    (f) 0-2 cobalt;
    (g) 0-15 indium;
    (h) 0-0.2 of a deoxidant selected from the group consisting of silicon, germanium, magnesium, aluminum, lithium, tantalum and mixtures thereof; and
    (i) 0-1.0 of a grain refiner selected from the group consisting of ruthenium, iridium, rhenium, and mixtures thereof, said alloy having a liquidus temperature of not more than 1400° C., said alloy having a tensile yield strength of at least 250 Mpa and an elongation of at least 2 percent.

2. The precious metal alloy in accordance with claim 1 wherein tin is present in an amount of 8-12 percent.

3. The precious metal alloy in accordance with claim 1 wherein boron is present in the amount of 0.03-0.1 percent.

4. The precious metal alloy in accordance with claim 1 wherein zinc is present in the amount of 3-7 percent.

5. The precious metal alloy in accordance with claim 1 wherein the grain refiner is present in the amount of 0.05-0.3 percent.

6. The precious metal alloy in accordance with claim 5 wherein said grain refiner is ruthenium.

7. The precious metal alloy in accordance with claim 1 wherein indium is present in the amount of 0.05-4.0 percent.

8. The precious metal alloy in accordance with claim 1 wherein silver is present in an amount of 8-12 percent.

9. The precious metal alloy in accordance with claim 1 wherein gold is present in an amount of 1-5 percent.

10. The precious metal alloy in accordance with claim 1 wherein gallium is present in an amount of 0.2-1.0 percent.

11. A precious metal alloy for dental restorations which develops a light oxide upon firing, said alloy, on a percentage weight basis at makeup, consisting essentially of:
    (a) 65-85 total amount of precious metal(s) selected from the group consisting of 65-72 palladium, 1-5 gold, 0-6 platinum, 8-12 silver, and mixtures thereof;
    (b) 8-12 tin;
    (c) 3-7 zinc;
    (d) 0.03-0.1 boron;
    (e) 0-2 gallium;
    (f) 0-2 cobalt;
    (g) 0.5-4.0 indium;
    (h) 0-0.2 of a deoxidant selected from the group consisting of silicon, germanium, magnesium, aluminum, lithium, tantalum and mixtures thereof; and
    (i) 0.05-0.3 of a grain refiner selected from the group consisting of ruthenium, iridium, rhenium, and mixtures thereof, said alloy having a liquidus temperature of not more than 1400° C., said alloy having a tensile yield strength of at least 250 Mpa and an elongation of at least 2 percent.

12. The precious metal alloy in accordance with claim 11 wherein said grain refiner is ruthenium.

13. The precious metal alloy in accordance with claim 11 wherein gallium is present in the amount of 0.2–1.0 percent.

14. A dental restoration including
    (a) a casting of a precious metal alloy having a light oxide after firing; and
    (b) a translucent porcelain coating fired on said casting, said coating evidencing a light coloration, said alloy, on a percentage weight basis at makeup, consisting essentially of:
    (i) 60–95 total amount of precious metal(s) selected from the group consisting of 60–85 palladium, 0–5 gold, 0–10 platinum, 0–12 silver, and mixtures thereof;
    (ii) 1–15 tin;
    (iii) 2–7 zinc;
    (iv) 0,005–0.2 boron;
    (v) 0–2 gallium;
    (vi) 0–2 cobalt;
    (vii) 0–15 indium;
    (viii) 0–0.2 of a deoxidant selected from the group consisting of silicon, germanium, magnesium, aluminum, lithium, tantalum and mixtures thereof; and
    (ix) 0–1.0 of a grain refiner selected from the group consisting of ruthenium, iridium, rhenium, and mixtures thereof, said alloy having a liquidus temperature of not more than 1400° C., said alloy having a tensile yield strength of at least 250 Mpa and an elongation of at least 2 percent.

15. The dental restoration in accordance with claim 14 wherein said alloy, at makeup, includes 8–12 percent tin, 2–4 percent zinc and 0.03–0.1 percent boron.

16. The dental restoration in accordance with claim 14 wherein said alloy, at makeup, includes 0.2–1.0 percent gallium.

17. The dental restoration in accordance with claim 14 wherein said alloy, at makeup, includes 8–12 percent silver and 1–5 percent gold.

18. The dental restoration in accordance with claim 14 wherein said alloy, at makeup, includes 0.05–0.3 percent of the grain refiner.

19. The dental restoration in accordance with claim 18 wherein said grain refiner is ruthenium.

* * * * *

UNITED STATES PATENT AND TRADEMARK OFFICE
CERTIFICATE OF CORRECTION

PATENT NO. : 5,431,875
DATED : July 11, 1995
INVENTOR(S) : Thomas B. Cameron et al It is certified that error appears in the above-indentified patent and that said Letters Patent is hereby corrected as shown below:

Column 7, line 23, delete "0,005" and insert --0.005--.

Signed and Sealed this

Twenty-fourth Day of October, 1995

*Attest:*

BRUCE LEHMAN

*Attesting Officer*  *Commissioner of Patents and Trademarks*